United States Patent [19]

Sitzmann et al.

[11] Patent Number: 5,155,281
[45] Date of Patent: Oct. 13, 1992

[54] PREPARING DICHLOROFORMALS

[75] Inventors: Michael E. Sitzmann, Adelphi, Md.; William H. Gilligan, Ft. Washington, D.C.

[73] Assignee: The United States of America as represented by the Secretary of the Navy, Washington, D.C.

[21] Appl. No.: 640,187

[22] Filed: Jun. 1, 1984

[51] Int. Cl.$^5$ .............................................. C07C 43/30
[52] U.S. Cl. .................................... 568/590; 149/88; 568/594; 568/604
[58] Field of Search ............... 149/88; 568/590, 594, 568/604

[56] References Cited

U.S. PATENT DOCUMENTS

| | | | |
|---|---|---|---|
| 3,306,939 | 2/1967 | Hill | 260/644 |
| 3,922,311 | 11/1975 | Peters et al. | 568/590 |
| 3,937,738 | 2/1976 | Throckmorton | 568/41 |
| 4,120,710 | 10/1978 | Peters et al. | 149/88 |
| 4,172,088 | 10/1979 | Angres et al. | 558/243 |
| 4,323,518 | 4/1982 | Gilligan | 558/243 |
| 4,449,000 | 5/1984 | Sitzmann et al. | 149/88 |
| 4,499,309 | 2/1985 | Sitzmann et al. | 149/88 |

OTHER PUBLICATIONS

Gilligan, U.S. patent application Ser. No. 256,462, filed Mar. 30, 1981.

*Primary Examiner*—Edward A. Miller
*Attorney, Agent, or Firm*—Kenneth E. Walden; Roger D. Johnson

[57] ABSTRACT

A method of preparing dichloroformals of the formula $$(RCH_2O)_2CCl_2$$

by reaction of one mole of a thionocarbonate of the formula $$(RCH_2O)_2C=S$$

with two moles of benzenesulfenyl chloride, chlorobenzenesulfenyl chloride, or methanesulfenyl chloride wherein R is $-C(NO_2)_3$, $-CF(NO_2)_2$, $-CF_2(NO_2)$, $-CCl(NO_2)_2$, $-C(NO_2)_2CH_3$, $-CCl_3$, $-CF_3$, or $-CF_2CF_3$. These energetic dichloroformals are useful as explosive and propellant ingredients and as intermediates in the synthesis of other energetic explosive and propellant ingredients.

7 Claims, No Drawings

PREPARING DICHLOROFORMALS

BACKGROUND OF THE INVENTION

This invention relates to energetic organic compounds and more particularly to halo- and nitroalkyl dichloroformals.

U.S Pat. No. 3,306,939, entitled "Orthoesters of 2,2,2-Trinitroethanol," which issued to Marion E. Hill on Feb. 28, 1967, suggests bis(2,2,2-trinitroethyl) dichloroformal as a transitory intermediate in the synthesis of trinitroethyl orthocarbonate from 2,2,2-trinitroethanol and carbon tetrachloride in the presence of ferric chloride. The dichloroformal was neither isolated nor actually identified. Given the reactivity of the dichloroformal under those conditions, the method is unsuitable for the synthesis of bis(polynitroalkyl) dichloroformals.

Two methods for the preparation of polynitroethyl dichloroformals are described by W. H. Gilligan in U.S. patent application Ser. No. 256,462 which was filed on Mar. 30, 1981. The first method involves refluxing a thionocarbonate of the formula $(RCH_2O)_2C=S$ (where $R = -C(NO_2)_3, -CF(NO_2)_2, -CCl(NO_2)_2, -C(NO_2)_2CH_3, -CCl_3, -CF_3,$ and $-CF_2C_3$) with sulfuryl chloride in the presence of a Friedel-Crafts catalyst such as $AlCl_3$ or $TiCl_4$. This method has the disadvantage that stringent reaction conditions (refluxing sulfuryl chloride at 70° C. for 5 days) are required. The best yields are approximately 70%, but often yields are substantially lower since the reaction is sensitive to the choice of catalyst.

The second method for the preparation of polynitroethyl dichloroformals is treatment of the thionocarbonate with gaseous chlorine in a mixture of a chlorinated hydrocarbon and a polar additive (such as trifluoroethanol or acetonitrile). Although the polar additives are necessary for reaction to occur, they can cause problems due to their involvement in side reactions. Trifluoroethanol can react with dichloroformals (I) to give mixed 2:2 orthocarbonates (II).

$$(RCH_2O)_2CCl_2 \xrightarrow{CF_3CH_2OH} (RCH_2O)_2C(OCH_2CF_3)_2$$
$$\text{I} \qquad\qquad\qquad\qquad \text{II}$$

Thus care must be taken to minimize this side reaction by keeping reaction temperatures between 15° and 25° C. Care must also be taken during the isolation of the dichloroformal product to avoid formation of appreciable amounts of the mixed 2:2 orthocarbonate. This appreciable side reaction not only lowers the yield, but causes difficulty in the isolation of the pure dichloroformal. When acetonitrile is employed as the polar additive, side reactions can also occur. Upon prolonged exposure to the sulfur chloride byproducts formed in the reaction, acetonitrile reacts to give a black polymeric substance which cannot be removed from the dichloroformal. Thus it is critical to closely monitor reaction times to avoid formation of appreciable amounts of this impurity.

Therefore, it would be desirable to provide an improved method of preparing halo-, nitro-, and halonitroalkyl dichloroformals.

SUMMARY OF THE INVENTION

Accordingly, an object of this invention is to provide a new method of preparing halo-, nitro-, and halonitroalkyl dichloroformals.

Another object of this invention is to provide a method of preparation which produces halo-, nitro-, and halonitroalkyl dichloroformals in greater yields.

A further object of this invention is to provide a method of producing halo-, nitro-, and halonitroalkyl dichloroformals using mild reaction conditions.

Yet another object of this invention is to provide a method of producing halo-, nitro-, and halonitroalkyl dichloroformals in which the products are more easily isolated and purified.

These and other objects of this invention are accomplished by providing a method of preparing dichloroformals of the formula $$(RCH_2O)_2CCl_2$$

by reacting a thionocarbonate of the formula $$(RCH_2O)_2C=S$$

with benzenesulfenyl chloride, chlorobenzenesulfenyl chloride, or methanesulfenyl chloride, wherein $R = -C(NO_2)_3, -CF(NO_2)_2, -CF_2(NO_2), -CCl(NO_2)_2, -C(NO_2)_2CH_3, -CCl_3, -CF_3,$ or $-CF_2CF_3$.

DETAILED DESCRIPTION OF THE INVENTION

Thionocarbonates of the formula $$[C(NO_2)_3CH_2O]_2C=S,$$

$$[CF(NO_2)_2CH_2O]_2C=S,$$

$$[CF_2(NO_2)CH_2O]_2C=S,$$

$$[CCl(NO_2)_2CH_2O]_2C=S,$$

$$[CH_3C(NO_2)_2O]_2C=S,$$

$$[CCl_3CH_2O]_2C=S,$$

$$[CF_3CH_2O]_2C=S, \text{ and}$$

$$[CF_3CF_2CH_2O]_2C=S, \text{ are}$$

used to synthesis dichloroformals of the formula $$[C(NO_2)_3CH_2O]_2CCl_2,$$

$$[CF(NO_2)_2CH_2O]_2CCl_2,$$

$$[CF_2(NO_2)CH_2O]_2CCl_2,$$

$$[CCl(NO_2)_2CH_2O]_2CCl_2,$$

$$[CH_3C(NO_2)_2O]_2CCl_2,$$

$$[CCl_3CH_2O]_2CCl_2,$$

$$[CF_3CH_2O]_2CCl_2, \text{ and}$$

$$[CF_3CF_2CH_2O]_2CCl_2,$$

respectively.

In the method of this invention, one mole of the appropriate thionocarbonate reacts with two moles of benzenesulfenyl chloride (or other sulfenyl chlorides of similar reactivity such as chlorobenzenesulfenyl chloride or methanesulfenyl chloride) to produce the desired dichloroformal:

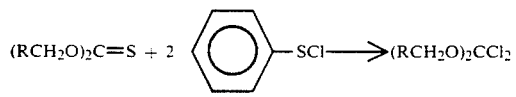

(wherein R=—C(NO$_2$)$_3$, CF(NO$_2$)$_2$, —CCl(NO$_2$)$_2$, —C(NO$_2$)$_2$CH$_3$, —CCl$_3$, —CF$_3$, and CF$_2$CF$_3$).

The reaction requires a minimum of 2 moles of benzenesulfenyl chloride per mole of thionocarbonate and proceeds under mild conditions (e.g., normal room temperature and pressure) without side reactions or need of catalyst to give excellent yields of dichloroformal. Benzenesulfenyl chloride, chlorobenzenesulfenyl chloride, and methanesulfenyl chloride may be used, with benzenesulfenyl chloride being preferred.

A preferred reaction temperature range is from 15° C. to about 100° C., with from 15° C. to 30° C. being more preferred.

When solvent is required, a polar solvent such as nitromethane, nitroethane, or nitrobenzene is preferred, but chlorinated hydrocarbons such as methylene chloride, chloroform, 1,1-dichloroethane, 1,2-dichloroethane, or 1,1,2-trichloroethane can also be used. The reaction rate is slower, however, in the halocarbon solvents. Solvents that react with the sulfenyl chlorides are not suitable. Thus ethers, DMSO, acetone, THF, etc., can not be used as the reaction solvent. For liquid thionocarbonates the reaction can be carried out without solvent by slowly adding neat benzenesulfenyl chloride.

The dichloroformal can be readily isolated in excellent yield from the sulfur containing byproducts by crystallization or distillation procedures. Example 2, illustrates the isolation of a solid dichloroformal product by crystallization from carbon tetrachloride and 1,2dichloroethane with cooling (5° C.). Example 3, illustrates the isolation of a liquid product dichloroformal by vacuum distillation.

A method of synthesizing the bis(2-fluoro-2,2-dinitroethyl)thionocarbonate is disclosed in Example 1 of U.S. Pat. No. 4,172,088, entitled "Bis(2-fluoro-2,2-dinitroethyl)thionocarbonate and a Method of Preparation," which issued to Angres et al on Oct. 23, 1979, herein incorporated by reference. The remaining thionocarbonate starting materials may be prepared by the method disclosed in U.S. Pat. No. 4,323,518, entitled "Polynitroethylthionocarbonates and Method of Preparation," which issued to William H. Gilligan on Apr. 6, 1982, herein incorporated by reference.

To more clearly illustrate this invention, the following examples are represented. It should be understood, however, that these examples are presented merely as a means of illustration and are not intended to limit the scope of the invention in any way.

EXAMPLE 1

Bis(2-fluoro-2,2-dinitroethyl) dichloroformal

To a solution of 3.3 g (0.0227 mole) of benzenesulfenyl chloride in 4 ml of dry nitromethane was added 3.0 g (0.0086 mole) of bis(2-fluoro-2,2-dinitroethyl) thionocarbonate. After 5 days at 25° C., the volatiles (mainly nitromethane) were removed at 30° C. under reduced pressure (vacuum pump). The residue solidified and was stirred with dry hexane to give 3.0 g (90%), mp 55°–57° C. The H-NMR spectrum was identical to that of authentic bis(2-fluoro-2,2-dinitroethyl) dichloroformal.

EXAMPLE 2

Bis(2,2-dinitropropyl) dichloroformal

A solution of 9.6 g (0.066 mole) of benzenesulfenyl chloride in 7 ml of dry nitromethane was stirred at 25° C while 7.55 g (0.022 mole) of bis(2,2-dinitropropyl) thionocarbonate was added. After 24 hours, the nitromethane was removed at 30° C. under reduced pressure (vacuum pump). The product was stirred with 25 ml of dry carbon tetrachloride, and the mixture was cooled to 5° C. to give 7.75 g (92%), mp 122°–127° C. Crystallization from 1,2-dichloroethane gave 7.2 g (86%), mp 126°–128° C. The mixed melting point with authentic bis(2,2-dinitropropyl) dichloroformal as well as H-NMR confirmed the product to be the dichloroformal.

EXAMPLE 3

Bis(2,2,2-trifluoroethyl) dichloroformal

Benzenesulfenyl chloride (11.4 g) (0.079 mole) was slowly added in portions with stirring to 7.9 g (0.033 mole) of bis(2,2,2-trifluoroethyl) thionocarbonate. The reaction was slightly exothermic, and two phases were present after 1.5 hours. The mixture was allowed to stand overnight before it was distilled, and the liquid boiling at 49° C. (51 mm) was collected. The yield was 7.81 g (85%). The H-NMR spectrum was identical to an authentic sample of bis(2,2,2-trifluoroethyl) dichloroformal.

Obviously, many modifications and variations of the present invention are possible in light of the above teachings. It is therefore to be understood that within the scope of the appended claims the invention may be practiced otherwise than as specifically described.

What is claimed is:

1. A method of synthesizing dichloroformals of the formula

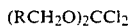

by reacting each mole of a thionocarbonate of the formula

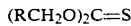

with two moles of a sulfenyl chloride selected from the group consisting of benzenesulfenyl chloride, chlorobenzenesulfenyl chloride, and methanesulfenyl chloride wherein R is selected from the group consisting of —C(NO$_2$)$_3$, —CF(NO$_2$)$_2$, —CF$_2$(NO$_2$), —CCl(NO$_2$)$_2$, —C(NO$_2$)$_2$CH$_3$, —CCl$_3$, —CF$_3$, and —CF$_2$F$_3$.

2. The method of claim 1 wherein the sulfenyl chloride is benzenesulfenyl chloride.

3. The method of claim 1 wherein the reaction is run at a temperature of from about 15° C. to about 100° C.

4. The method of claim 3 which is run at a temperature of from 15° C. to 30° C.

5. The method of claim 1 wherein a polar solvent selected from the group consisting of nitromethane, nitroethane, and nitrobenzene is used as a solvent.

6. The method of claim 5 wherein the polar solvent is nitromethane.

7. The method of claim 1 wherein a chlorinated hydrocarbon selected from the group consisting of chloroform, methylene chloride, 1,1-dichloroethane, 1,2-dichloroethane, 1,1,2-trichloroethane, and mixtures thereof is used as a solvent.

* * * * *